(12) United States Patent  
Röhner

(10) Patent No.: US 6,679,101 B1  
(45) Date of Patent: Jan. 20, 2004

(54) DEVICE FOR DETECTING LEAKAGE IN MEMBRANES

(75) Inventor: Gerhard Röhner, Hemsbach (DE)

(73) Assignee: Carl Freudenberg KG, Weinheim (DE)

( * ) Notice: Subject to any disclaimer, the term of this patent is extended or adjusted under 35 U.S.C. 154(b) by 0 days.

(21) Appl. No.: 10/009,905

(22) PCT Filed: Jun. 13, 2000

(86) PCT No.: PCT/EP00/05422

§ 371 (c)(1), (2), (4) Date: Jul. 2, 2002

(87) PCT Pub. No.: WO01/14844

PCT Pub. Date: Mar. 1, 2001

(30) Foreign Application Priority Data

Jun. 10, 1999 (DE) .......................................... 199 26 372

(51) Int. Cl.[7] .................... G01N 15/08; G01M 3/04; H01H 29/00; H01H 35/42; G08B 21/00
(52) U.S. Cl. ........................... 73/38; 73/40; 200/61.04; 200/61.06; 340/604
(58) Field of Search ...................... 73/40, 40.5, 38; 340/604, 605; 200/61.04, 61.05, 61.06; 174/11 R

(56) References Cited

U.S. PATENT DOCUMENTS

| 2,432,367 | A | * | 12/1947 | Andresen ................. 200/61.04 |
| 3,427,414 | A | * | 2/1969 | Sheldahl .................. 200/61.04 |
| 3,562,731 | A | * | 2/1971 | Hsu .......................... 340/604 |
| 4,246,575 | A | * | 1/1981 | Purtell et al. ............... 340/605 |
| 4,926,165 | A |   | 5/1990 | Lahlouh et al. |
| 5,329,081 | A | * | 7/1994 | Jones ...................... 200/61.04 |

FOREIGN PATENT DOCUMENTS

| EP | 0 715 690 | 9/1997 |
| JP | 62-294939 | 12/1987 |
| WO | 95/06205 | 3/1995 |

* cited by examiner

*Primary Examiner*—Michael Cygan  
(74) *Attorney, Agent, or Firm*—Kenyon & Kenyon

(57) ABSTRACT

A device for detecting leaks in membranes, etc., for liquid media, whereby the membrane is provided, over at least one partial area of its surface extension, with at least one electrical conductor that produces a change in a measurement signal of the electrical resistance of the conductor when a change occurs on the membrane surface, the membrane being provided with a swellable nonwoven that joins or separates the conductors when influenced by the liquid.

14 Claims, 5 Drawing Sheets

DEVICE FOR DETECTING LEAKAGE IN MEMBRANES

FIELD OF THE INVENTION

The present invention relates to a device for detecting leaks in membranes, etc., for liquid media, whereby the membrane is provided, over at least one partial area of its surface extension, with at least one electrical conductor that produces a change in a measurement signal of the electrical resistance of the conductor when a change occurs on the membrane surface.

BACKGROUND INFORMATION

Devices of this type are used primarily where liquids are separated from the external environment by membranes, or where membranes are used to conduct liquids. Such applications frequently have very high liquid purity requirements, and the liquid is protected against all possible contamination. This is the case, for example, in the treatment of food, chemicals and other liquids.

A flexible pump membrane that is made of one or more layers of a flexible material is described in European Published Patent Application No. 0 715 690, where one layer is made of a compressed porous polytetrafluoroethylene, in which is embedded an electrically conductive fiber made of an expanded porous polytetrafluoroethylene. The conductive fiber is connected to a monitoring device, and the state of the membrane is monitored by measuring changes in conductivity. However, a membrane of this type, having a fiber embedded in the PTFE layer, is difficult and expensive to manufacture.

SUMMARY

It is an object of the present invention to provide a device for detecting leaks in membranes, etc., which is as economical as possible and provides a reliable reading even with very small leaks in the membrane.

According to the general concept of the present invention, therefore, the membrane is provided with a swellable nonwoven that swells when influenced by the liquid through cracks, etc., in the membrane and either joins or separates the electrical conductors provided on the membrane. The conductors are not provided in the membrane itself, but are located on top of the membrane. According to an example embodiment of the membrane, the latter is constructed like a sandwich with at least two layers, and the conductors embedded between two adjacent layers. The conductors may be arranged above one another and separated by an insulator. Depending on whether the swellable nonwoven is to join or separate the conductors, the swellable nonwoven is made of an electrically conductive or nonconductive material.

The swellable nonwoven itself may be inserted as a parallel layer relative to the membrane layers. According to one example embodiment, the membrane is made of an elastomer layer and a PTFE layer, between which the swellable nonwoven and the conductors are embedded, with the swellable nonwoven being adjacent to the PTFE layer.

The foregoing object may be achieved by configuring one conductor as an unbroken surface and the other conductor as a perforated surface. In this case, for example, the membrane layer facing the liquid may be made of PTFE on which a swellable nonwoven is provided. On the swellable nonwoven is placed a first conductor with a perforated surface, followed by an insulating layer with the same perforations. The second conductor with an unbroken surface is provided next, followed by an elastomer layer. The device constructed in this manner is equipped with an electrically conductive swellable nonwoven which swells upon penetration by liquid and enters the perforations in the first conductor and in the insulator until it comes into contact with the second conductor. The two conductive layers of the conductor are joined in this manner, and the corresponding monitoring device displays this state.

According to another example embodiment, the conductors are formed by unbroken surfaces in both layers, with each consecutive surface segment of the conductors contacting each other like bridges so that both conductor layers are joined in an electrically conductive manner. At least in the case of one of the conductors, the spaces between the surface segments are filled with the swellable nonwoven. This swellable nonwoven is made of a nonconductive material. The swellable nonwoven swells as soon as it comes into contact with the liquid and thus separates the two conductor layers, with this state being displayed on the monitoring device.

A device of this type is constructed from a PTFE membrane layer on which is provided a first conductor having surface segments, with swellable nonwoven being inserted between the surface segments, and a second conductor that connects the surface segments like a bridge, after which follows an elastomer membrane layer.

The device according to the present invention is easily manufactured by joining the individual layers, i.e., conductor layers, and gluing or vulcanizing them together. A membrane of this type is also highly resistive as well as being enormously flexible.

DETAILED DESCRIPTION

Figure 1:
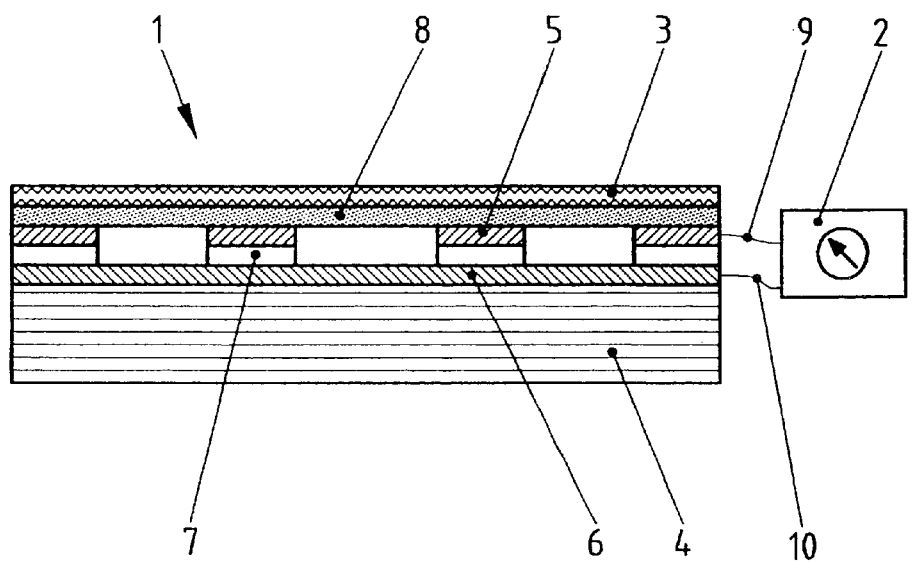
FIG. 1 is a cross-sectional view of the structure of an intact membrane with an electrically conductive swellable nonwoven.
Figure 2:
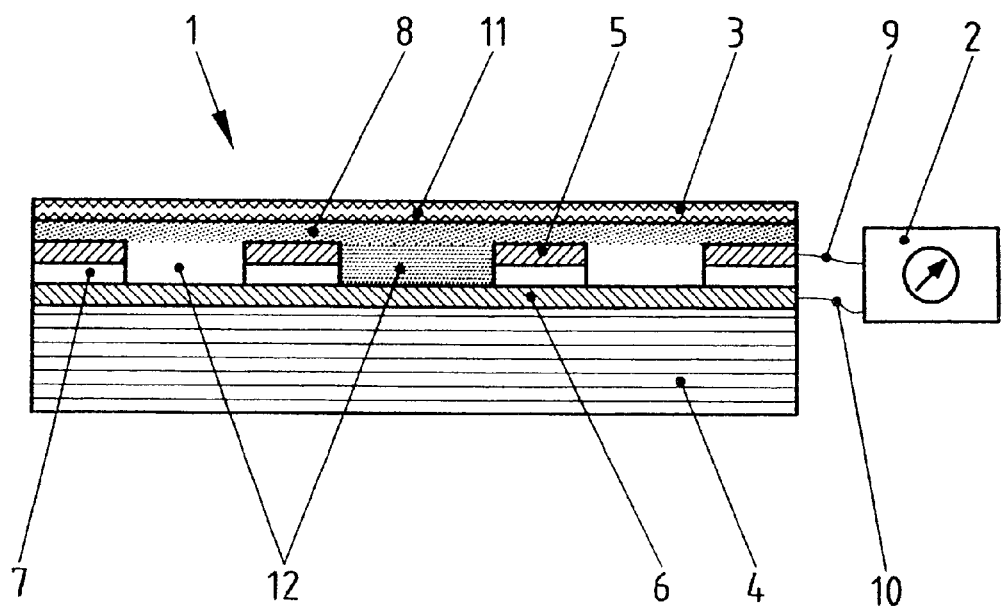
FIG. 2 illustrates the membrane illustrated in FIG. 1 with a leak.

The device illustrated in FIG. 1 for detecting leaks in a membrane includes membrane 1, constructed like a sandwich, and measuring unit 2 for detecting measurement signals. Membrane layer 3 facing the liquid is made of PTFE, while membrane layer 4 facing away from the liquid is an elastomer layer. Electrical conductors 5 and 6 are provided between the two membrane layers 3 and 4. Conductors 5 and 6 are separated by insulator 7. Conductor 6 is an unbroken surface that is provided as a layer on membrane layer 4 which is made of an elastomer. Conductor 5 has a perforated surface and is configured in the form of a screen. Insulator 7, which is located between conductors 5 and 6, has the same configuration. Swellable nonwoven 8 directly follows PTFE membrane layer 3 and is provided as a layer on PTFE membrane 3. Swellable nonwoven 8 is made of an electrically conductive material. Conductors 5 and 6 are connected to measuring unit 2 via connections 9 and 10. As soon as a leak occurs at any point on membrane layer 3, and liquid reaches swellable nonwoven 8, the latter swells immediately. A swelling layer measuring 0.5 mm, for example, swells approximately 20 times its size to roughly 11 mm in a very short period of time. As illustrated in FIG. 2, this swelling action joins the two conductors 5 and 6, thus producing a change in the electrical resistance between conductors 5 and 6, which is displayed accordingly on measuring unit 2. All components illustrated in FIG. 2 are identical to those illustrated in FIG. 1. The only difference is that a crack has occurred at point 11 in PTFE membrane layer 3, and liquid has reached swellable nonwoven layer 8. Swellable nonwoven layer 8 has swelled and filled open perforations 12 in the layers of conductor 5 and insulator 7, producing the change in resistance mentioned above.

The material and structural arrangement of membrane layers 3 and 4 as well as swellable nonwoven 8 and conductors 5, 6 are selected according to the application of membrane 1. In the present example embodiment, the PTFE membrane layer provides maximum resistance to chemical corrosion. At the same time, significantly thicker elastomer membrane layer 4, which in the example embodiment is four times the thickness of PTFE membrane layer 3, lends membrane 1 a high degree of elasticity and a long service life. Furthermore, this layered structure of membrane 1 provides a high level of safety, since leaks in PTFE membrane layer 3 are detectable at an early stage without allowing liquid to reach the outside. In this regard, elastomer membrane layer 4 provides a particularly high level of safety, for it acts as a second barrier, preventing liquid outflow over a large area.

Figure 3:
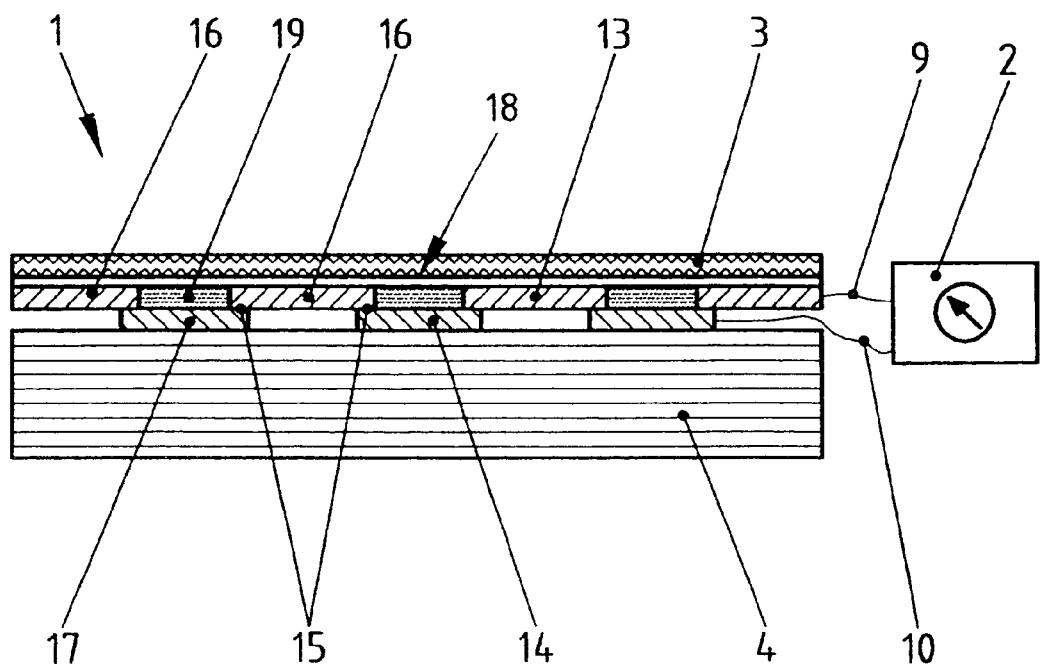
FIG. 3 is a cross-sectional view of the structure of an intact membrane with a nonconductive swellable nonwoven.
Figure 4:
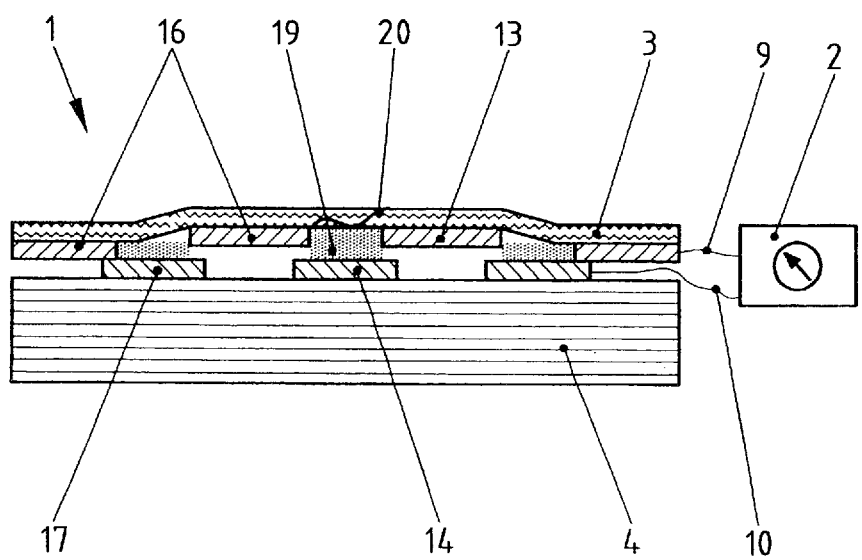
FIG. 4 illustrates the membrane illustrated in FIG. 3 with damage.

FIGS. 3 and 4 illustrate a different example embodiment of membrane 1. The sandwich-like structure of membrane 1, with a first membrane layer 3 made of PTFE and a second membrane layer 4 made of an elastomer, remains the same. Conductors 13 and 14, which are also in the form of layers, are inserted between the two membrane layers 3 and 4. Conductors 13 and 14 include consecutive surface segments that overlap and contact each other like bridges. The overlaps occur at points 15. Individual surface segments 16 and 17 of individual conductors 13 and 14 are approximately the same size in the present example embodiment. Conductor 13 is immediately adjacent to membrane layer 3. Spaces 18 present between individual surface segments 16 are filled with swellable nonwoven 19. Conductor 14 is followed by membrane layer 4, which is made of an elastomer. FIG. 4 illustrates a situation in which liquid has reached swellable nonwoven 19 through a crack 20 in membrane layer 3. Swellable nonwoven 19 has swelled at the corresponding point, separating the two conductors 13 and 14 from each other. The corresponding change in resistance may be read on measuring unit 2. Conductor 13 is permanently attached to membrane layer 3, and conductor 14 to membrane layer 4.

Figure 5:
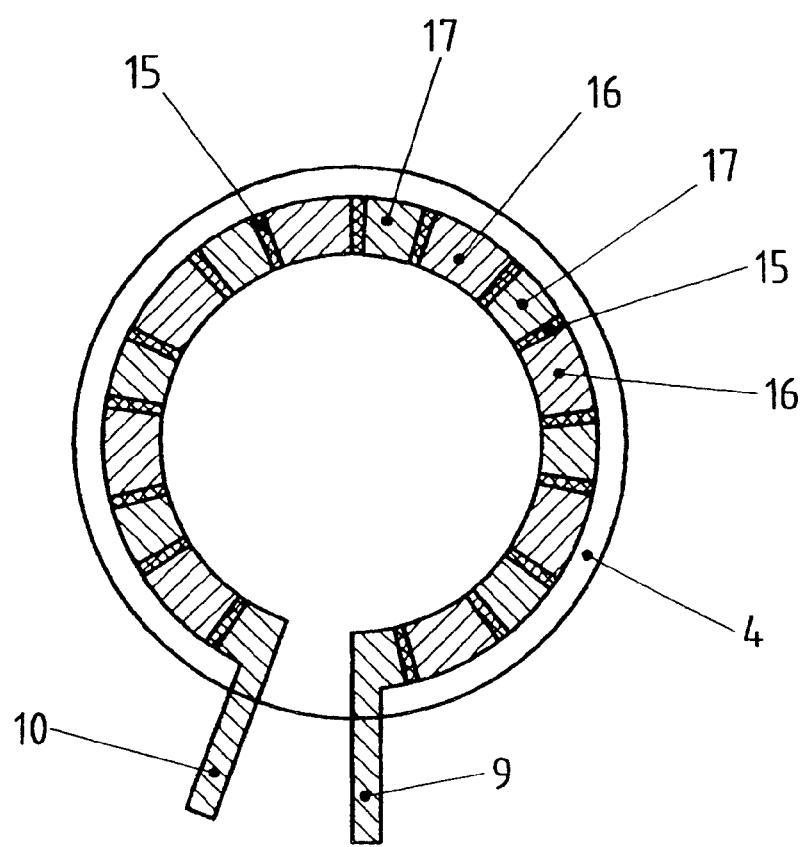
FIG. 5 is a top view of the membrane illustrated in FIGS. 3 and 4.

FIG. 5 is a top view of the arrangement of individual surface segments 16 and 17 relative to each other. Individual surface segments 17 belonging to conductor 14 are provided on membrane layer 4. Conductor 13 with individual surface segments 16 is provided on top of this arrangement like a bridge. Surface segments 16 and 17 overlap each other at points 15.

What is claimed is:

1. A device for detecting leaks in membranes for liquid media, comprising:
   at least one insulator interposed between two electrical conductors, the conductors provided over at least one partial area of a surface extension of the membrane, the electrical conductors configured to produce a change in a measurement signal of an electrical resistance of the conductors when a change occurs on the membrane surface, the membrane including a swellable nonwoven that one of joins and separates the conductors when influenced by the liquid.

2. The device according to claim 1, wherein the membrane includes a sandwich construction having at least two membrane layers, the conductors embedded between two adjacent membrane layers.

3. The device according to claim 1, wherein the conductors are arranged above one another.

4. A device for detecting leaks in membranes for liquid media, comprising:
   at least one electrical conductor provided over at least one partial area of a surface extension of the membrane, the electrical conductor configured to produce a change in a measurement signal of an electrical resistance of the conductor when a change occurs on the membrane surface;
   the membrane including an electrically conductive swellable nonwoven that one of joins and separates the conductors when influenced by the liquid;
   wherein the conductors are separated by at least one insulator.

5. The device according to claim 1, wherein the swellable nonwoven is electrically conductive.

6. The device according to claim 2, wherein the swellable nonwoven is arranged as a parallel layer relative to the membrane layers.

7. A device for detecting leaks in membranes for liquid media, comprising:
   at least one electrical conductor provided over at least one partial area of a surface extension of the membrane, the electrical conductor configured to produce a change in a measurement signal of an electrical resistance of the conductor when a change occurs on the membrane surface;
   the membrane including a swellable nonwoven that one of joins and separates the conductors when influenced by the liquid;
   wherein the membrane includes a PTFE membrane layer and an elastomer membrane layer.

8. The device according to claim 7, wherein the swellable nonwoven is arranged adjacent to the PTFE membrane layer.

9. A device for detecting leaks in membranes for liquid media, comprising:
   a first and a second electrical conductor provided over at least one partial area of a surface extension of the membrane, the electrical conductor configured to produce a change in a measurement signal of an electrical resistance of the conductor when a change occurs on the membrane surface;
   the membrane including a swellable nonwoven that one of joins and separates the conductors when influenced by the liquid;
   wherein the first conductor is configured as an unbroken surface and the second conductor is configured as a perforated surface.

10. The device according to claim 7, further comprising a perforated insulating layer, wherein the swellable nonwoven is provided on the PTFE membrane layer in the form of a layer, a first conductor includes a perforated surface, and a second conductor includes an unbroken surface.

11. The device according to claim 10, wherein perforations in the insulating layer and perforations in the first conductor are identical.

12. A device for detecting leaks in membranes for liquid media, comprising:
   at least one electrical conductor provided over at least one partial area of a surface extension of the membrane, the electrical conductor configured to produce a change in a measurement signal of an electrical resistance of the conductor when a change occurs on the membrane surface;
   the membrane including a swellable nonwoven that one of joins and separates the conductors when influenced by the liquid, wherein the at least one conductor includes two conductors, each conductor formed by surface segments, each consecutive surface segment contacting each other in a bridge manner, a space between surface segments of at least one conductor filled with the swellable nonwoven.

13. A device for detecting leaks in membranes for liquid media, comprising:
   at least one electrical conductor provided over at least one partial area of a surface extension of the membrane, the electrical conductor configured to produce a change in a measurement signal of an electrical resistance of the conductor when a change occurs on the membrane surface;
   the membrane including a swellable nonwoven that one of joins and separates the conductors when influenced by the liquid;
   a PTFE membrane layer and an elastomer layer, an adjoining first conductor including surface segments having the swellable nonwoven arranged therebetween, a second conductor connecting the surface segments in a bridge manner.

14. A device for detecting leaks in membranes for liquid media, comprising:
   at least one electrical conductor provided over at least one partial area of a surface extension of the membrane, the electrical conductor configured to produce a change in a measurement signal of an electrical resistance of the conductor when a change occurs on the membrane surface;
   the membrane including a swellable nonwoven that one of joins and separates the conductors when influenced by the liquid;
   wherein individual layers of the membrane are joined by one of gluing and vulcanization.

* * * * *